United States Patent [19]

Hamada

[11] Plant 4,674

[45] Mar. 17, 1981

[54] NECTARINE TREE

[75] Inventor: Hajime Hamada, Kingsburg, Calif.

[73] Assignees: Robert M. Hamada; Lindsay K. Hamada, both of Kingsburg, Calif.

[21] Appl. No.: 96,987

[22] Filed: Nov. 23, 1979

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Huebner & Worrel

[57] ABSTRACT

A nectarine tree broadly bearing yellow-fleshed fruit of large size and resembling the Sun Grand Variety (U.S. Plant Pat. No. 974), but which bears fruit which attains an overall red coloration without exposure to sun, which ripens evenly, and which ripens about one week earlier than that of the Sun Grand.

1 Drawing Figure

BACKGROUND OF THE VARIETY

The present invention relates to a new and distinct variety of nectarine tree which is broadly similar to the Sun Grand Nectarine Tree (U.S. Plant Pat. No. 974), of which it is believed to be a mutant, in bearing yellow-fleshed, free-stone fruit of large size but from which it differs in bearing fruit which ripens substantially all at the same time and about one week earlier than that of the Sun Grand variety and which attains an overall full red coloration even when not fully exposed to the sun.

The Sun Grand variety of nectarine tree is well known in commercial plantings of nectarine trees as a productive bearer of midseason ripening reddish-skinned fruit. However, despite its success this variety is disadvantageous in that its fruit ripens unevenly so that it is not possible to harvest all of the fruit of this variety at one time. The fruit borne by the Sun Grand variety does not attain a full red coloration except on those portions exposed to the sun. This is disadvantageous with fruit such as nectarines whose purchase by consumers is largely influenced by exterior coloration, especially since other varieties of nectarine trees, such as the early-ripening May Grand variety (U.S. Plant Pat. No. 2,794) bear fruit which is more evenly colored, although smaller in size.

It has been recognized as desirable to provide a nectarine tree bearing fruit of large size which can be marketed in midseason but which ripens evenly and has a superior coloration to that of the Sun Grand variety in being red substantially overall. It is especially desirable to provide a nectarine tree with these characteristics which bears fruit ripening earlier than that borne by the Sun Grand variety.

The subject variety also bears some similarity to the nectarine tree of U.S. Plant Pat. No. 4,141 but is distinguished therefrom in blooming approximately 10 days earlier, bearing fruit which is more uniformly red even along its suture, bearing fruit which ripens from 2 to 15 days earlier, and fruit which colors substantially uniformly even in the shade.

ORIGIN AND ASEXUAL REPRODUCTION OF THE NEW VARIETY

The new variety of nectarine tree was discovered by me in 1974 as a mutant growing in an orchard of Sun Grand nectarine trees owned by me and located at the Northeast corner of Floral and Smith Avenues near the City of Reedley, in the County of Fresno in the State of California.

The mutation was asexually reproduced by whip grafting into trees by an employee of mine under my supervision at a ranch owned by me and located at 15958 East Rose Avenue near the City of Kingsburg in the County of Fresno in the State of California. The fruit and tree characteristics resulting from this grafting proved identical to those of the original mutation.

SUMMARY OF THE NEW VARIETY

The instant variety of nectarine tree is characterized by perpetuating the general characteristics of the Sun Grand Nectarine Tree as in its bearing of yellow-fleshed, freestone fruit of large size, but is distinguished therefrom as to novelty by the even ripening of its fruit which ripens about one week earlier than that of the Sun Grand variety and by each fruit attaining a full red coloration overall even though not evenly exposed to the sun.

The new nectarine tree bears fruit whose skin attains a color of Brickdust (Plate 5-L-11) substantially overall on a ground color of Forsythia (Plate 9-K-6), which has an average ripening date of June 29 or 30, and which is substantially uniformly sized with an averge diameter of 61 to 62 mm.

BRIEF DESCRIPTION OF THE DRAWING

The accompanying drawing is a color photograph of four mature nectarines of the subject variety with one of the fruits divided along the suture plane to show the flesh color and stone characteristics, together with representative twigs bearing characteristic leaves.

DETAILED DESCRIPTION

Referring more specifically to the pomological details of the new and distinct variety of nectarine tree, the following has been observed under the ecological conditions prevailing in the designated orchard in Fresno County, Calif. All color code plate identifications are by reference to the A. Maerz and M. Paul Dictionary of Color, Second Edition 1950.

TREE

Size: Large.

Figure: Spreading.

Productivity: Medium productive.

Regularity of bearing: Regular.
Trunk:
*Diameter in relation to length.*—Stocky.
*Surface characteristics.*—Medium.
Branches:
*Size.*—Stocky.
*Surface character.*—Medium.
*Color.*—Guinea Hen, Plate 16-E-4.
*Lenticels.*—Number — Numerous. Size — 1 mm.×4–5 mm.
Leaves:
*Size.*—Medium.
*Length.*—140 mm.
*Width.*—40 mm.
*Shape.*—Lanceolate.
*Color.*—Upperside — Privet, Plate 24-L-5. Lowerside — Elm Green, Plate 23-J-5.
*Marginal form.*—Finely serrate.
*Glandular characteristics.*—Reniform, two opposite each other.
*Petiole.*—Length — 12 mm. Thickness — 2 mm.
*Stem glands.*—Number — 2 to 3. Arrangement — Alternate. Size — 1.5 mm.×0.5 mm. Type — Reniform. Color — Pekinese, Plate 13-K-10.
Buds:
*Size.*—Large.
*Shape.*—Obtuse and plump.
*Surface.*—Pubescent.
Flowers:
*Dates of bloom.*—First bloom noted Mar. 1, 1979; 90% open on Mar. 12, 1979; Petal fall noted Mar. 17, 1979.
*Size.*—Large, 25 mm. in diameter.
*Color.*—Upperside — Pink, Plate 49-D-1. Lowerside — Pink, Plate 49-E-1.
*Number of pistils and stamens.*—Pistils — 1. Stamens — 38 to 39.

FRUIT

Maturity: Harvest date of June 29 or 30.
Size:
*Uniformity.*—Uniform size.
*Diameter.*—61 to 62 mm.
Transverse in suture plane.—60 to 61 mm.
*Transverse at right angles to suture plane.*—61 to 63 mm.
Form:
*Symmetry.*—Round oblong with unequal sides.
*Suture.*—Distinct, slightly depressed overall with marked depression at pistil point. Same color as skin. Length — 90 mm.
*Ventral surface.*—Lipped throughout, lips unequal.
*Stem cavity.*—Acuminate, 10 mm.×15 mm.×10 mm. deep.
*Base.*—Oblique.
*Apex.*—Depressed.

*Pistil point.*—Mucronate.
*Stem.*—Length — 11 mm. Caliper — 4 mm.
*Skin.*—Thickness — Medium. Texture — Medium. Tendency to crack — Slight. Color: Blush — Brickdust, Plate 5-L-11. Ground color — Forsythia, Plate 9-K-6. Pubescence — None.
Flesh:
*Color.*—Jonquil, Plate 9-K-5.
*Color of pit well.*—Marguerite-Y, Plate 10-F-1.
*Juice.*—Juicy.
*Flavor.*—Pleasant.
*Aroma.*—Pleasant.
*Texture.*—Firm.
*Fibers.*—Fine.
*Ripening.*—Even.
*Eating quality.*—Good.
Stone: Free.
*Characteristic size.*—41 mm. long, 31 mm. breadth, 24 mm. thick.
*Form.*—Obovate.
*Surface.*—Pitted from base to center and irregularly furrowed from middle to apex.
*Sutures.*—Ventral — Thin with narrow groove throughout. Dorsal — Full, deep groove throughout.
*Ridges.*—Rounded near base and jagged near apex.
*Size and position of grooves.*—Narrow and shallow near base, wide and deep near apex.
*Color.*—Sunstone, Plate 12-G-12.
*Splitting tendency.*—Moderate.
Use: Fresh.
Keeping quality: Good.
Shipping quality: Good.

Although the new variety of nectarine tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of nectarine tree, what is new and desired to be secured by Letters Patent is:

1. A new and distinct variety of nectarine tree, substantially as illustrated and described, broadly characterized by bearing yellow-fleshed fruit of large size and by its general resemblance to the Sun Grand Nectarine Tree (U.S. Plant Pat. No. 974) of which it is believed to be a mutant but from which it is distinguished as to novelty by its fruit attaining an overall full red coloration even along its suture without overall exposure to sun, and by its fruit ripening substantially all at the same time and about one week earlier than the fruit of the Sun Grand.

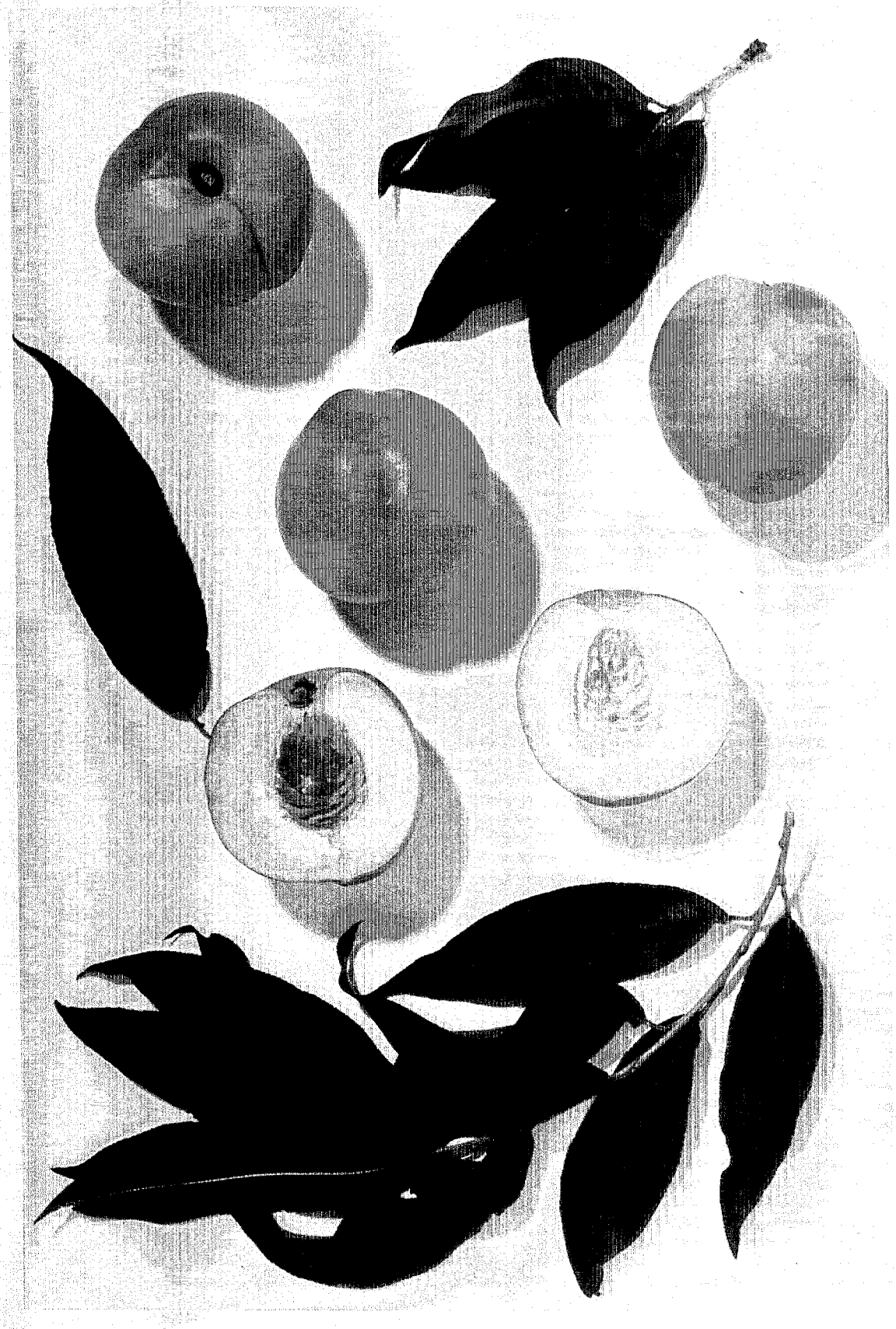

* * * * *